United States Patent [19]

Remy et al.

[11] Patent Number: 4,616,023

[45] Date of Patent: Oct. 7, 1986

[54] PHARMACEUTICAL COMPOSITIONS OF 4-(DIBENZO-[A,D]CYCLOALKENYL)PIPERAZINE COMPOUNDS AND METHODS

[75] Inventors: David C. Remy, North Wales; Steven D. Young, Lansdale, both of Pa.

[73] Assignee: Merck & Co., Inc., Rahway, N.J.

[21] Appl. No.: 703,965

[22] Filed: Feb. 21, 1985

Related U.S. Application Data

[63] Continuation-in-part of Ser. No. 596,957, Apr. 5, 1984, abandoned.

[51] Int. Cl.$^4$ .................................. A61K 31/445
[52] U.S. Cl. ................................................ 514/325
[58] Field of Search .......................... 514/404, 325

[56] References Cited

U.S. PATENT DOCUMENTS

| | | | |
|---|---|---|---|
| 3,167,541 | 1/1965 | van der Stelt | 568/808 |
| 4,091,023 | 5/1978 | Gerecke et al. | 424/250 |
| 4,105,664 | 8/1978 | Gerecke et al. | 424/250 |
| 4,144,337 | 3/1979 | Bastain | 424/25 |

OTHER PUBLICATIONS

Flaim et al., "Calcium Blockers", Urban & Schwarzenberg, publishers, pp. 37, 38, 129–133 (1982).
J. Med. Chem. 22 (2), 183(1979).

*Primary Examiner*—Douglas W. Robinson
*Attorney, Agent, or Firm*—Alice O. Robertson; William H. Nicholson; Michael C. Sudol

[57] ABSTRACT

Pharmaceutical compositions comprising 4-(dibenzo[a,d]cycloalkenyl)piperazine compounds and the use of said piperazine compounds for treatment of certain cardiovascular disorders are disclosed.

9 Claims, No Drawings

PHARMACEUTICAL COMPOSITIONS OF 4-(DIBENZO-[A,D]CYCLOALKENYL)PIPERAZINE COMPOUNDS AND METHODS

This application is a continuation-in-part application of U.S. Ser. No. 596,957 filed Apr. 5, 1984 now abandoned.

The present invention is directed to compositions comprising 4-(5H-dibenzo[a,d]cycloalkenyl)piperazine compounds and the use of said compounds in the treatment of certain cardiovascular disorders.

BACKGROUND OF THE INVENTION

It is known that calcium ions (Ca++) play vital roles in many cell processes. Calcium ions are particularly important to the function of cardiac tissue and vascular smooth muscle. The transition from the resting to the active state in the myocardium is initiated by cell depolarization which may be recorded as transmembrane action potential comprising a sharp peak caused by movement of sodium ions into the cell followed by a prolonged plateau during which calcium ions move into the cell. When intracellular concentrations of calcium ions rise above $10^{-7}$M, contraction occurs. The elevation of calcium ion concentration is believed to remove the inhibitory influence of the troponin-tropomyosin complex on the actin and the myosin necessary for contraction.

The movement of sodium and calcium ions into the cells is considered to be through "channels" in the cell membrane. The extent of influx of calcium ions appears to be dependent on the number of channels open and the extent of their opening. The extent of opening appears to be dependent on membrane depolarization, phosphorylation of certain protein kinases and activation of specific membrane receptors. The channels may be blocked by certain chemical compounds.

In view of the central role played by calcium ions in the electrophysiological and mechanical properties of the heart, and in the systemic and coronary arteries, the blocking of calcium ion channels can produce alterations in cardiovascular functions which can be advantageously employed in the treatment of a wide variety of cardiac disorders including cardiac arrhythmias, angina pectoris, arterial hypertension, hypertrophic obstructive cardiomyopathy and the like.

The effect of chemical compounds on the role played by calcium ions in cardiovascular functions is still being studied and suitable drugs are still being sought. Compounds which have been reported to be active as calcium entry blockers represent different types of chemical compounds. Thus, some of the drug names and their chemical names are as follows: Nifedipine, 1,4-dihydro-2,6-dimethyl-4-(2-nitrophenyl)-3,5-pyridinedicarboxylic acid dimethyl ester; Verapamil, α-[3-[2-(3,4-dimethoxyphenyl)-ethyl][methylamino]propyl]-3,4-dimethoxy-α-(1-methylethyl)benzeneacetonitrile; Prenylamine, N-(1-methyl-2-phenylethyl)-α-phenylbenzenepropanamine; Perhexiline, 2-(2,2-dicyclohexylethyl)-piperidine; Diltiazem, 3-(acetyloxy)-5-[2-(dimethylamino)-2,3-dihydro-2-(4-methoxyphenyl-1,5-benzothiazepin-4-(5H)-one; Cyproheptadine, 4-(5H-dibenzo[a,d]cyclohepten-5-ylidene)-1-methylpiperidine, and others.

Representative literature disclosing the foregoing compounds in calcium entry blocker activity include: D. A. Lowe et al., Br. J. Pharmacol. (1981) 74, 651; P. D. Henry, Am. J. Cardiology, 48, 1047 (1980); L. D. Hillis, J. Cardiovasc. Med. 5(6), 583, (1980); and R. A. Janis et al., J. Med. Chem. 26(6), 775 (1983).

A number of piperazines which are substituted on one nitrogen with a dibenzo[a,d]cycloalkenyl or analogous group, and on the other nitrogen with alkyl, cinnamyl, cinnamoyl, or carbalkoxy group have been reported to have pharmacological properties. The properties possessed by certain of the compounds are vesicatory (U.S. Pat. No. 3,357,982), psychostimulant (U.S. Pat. No. 4,144,337), antidepressant (British No. 1,127,354 and J. Med. Chem. 22, 183 (1979)) and antiulcer (British No. 1,029,920). None of these piperazine compounds are reported to have properties as calcium entry blockers.

DESCRIPTION OF THE INVENTION

According to the present invention it has been discovered that certain piperazine compounds represented by the formula

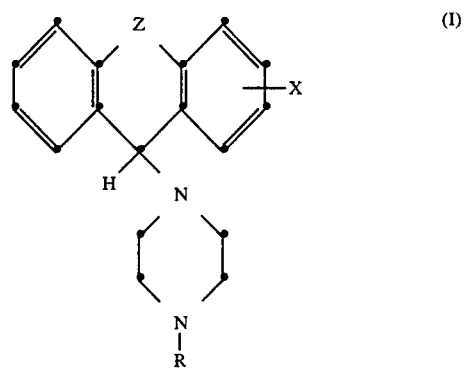

or a pharmaceutically acceptable acid addition salt thereof, or compositions containing said compounds are useful for treating cardiovascular disorders caused by high cellular concentration of Ca++. Some of the compounds are also useful as intermediates in the preparation of other pharmacologically active compounds.

In this and succeeding formulas,

X is hydrogen, halogen, lower alkoxy, lower alkylthio, or lower alkylsulfonyl, or trifluoromethyl, R is hydrogen, lower alkyl, cinnamyl, lower alkoxycinnamyl, cinnamoyl, lower alkoxycinnamoyl, lower hydroxyalkyl, of carbalkoxy, Z is a saturated or unsaturated 2 to 3 atom chain in which no more than one atom of the chain is other than carbon and which optionally may be substituted with 1 to 2 halogen atoms.

The atoms which are suitable in the 2 to 3 atom chain are carbon and either sulfur or oxygen. Representative saturated and unsaturated chains include —CH=CH—, —CH$_2$CH$_2$—, —CH$_2$CH$_2$CH$_2$—, —CH=CH—CH$_2$, —CH$_2$S— and —CH$_2$O—.

By "lower" when referring to alkyl, alkoxy, alkylthio and alkylsulfonyl is meant a group having from 1 to 6 carbon atoms. By "halogen" is meant any of the halogens: fluorine, chlorine, bromine and iodine.

The preferred compounds for the compositions and methods of the present invention are those in which Z is an unsaturated 2-carbon chain, R is lower alkyl, cinnamyl and lower alkoxycinnamyl and X is in the 3-position. These compounds may be represented by the formula:

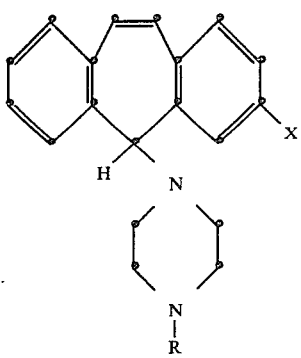

The acid addition salts are those of non-toxic, pharmaceutically acceptable acids and include salts of inorganic acids such as hydrochloric, hydrobromic, hydroiodic, phosphoric, sulfuric, nitric and the like, and organic acids such as acetic, propionic, glycolic, pamoic, pyruvic, malonic, succinic, maleic, fumaric, malic, tartaric, citric, mandelic, benzoic, cinnamic, methanesulfonic, ethanesulfonic, salicylic, p-toluenesulfonic, cyclohexanesulfamic, and the like and include acids related to the pharmaceutically acceptable salts listed in Journal of Pharmaceutical Sciences, 66, 2 (1977) and incorporated herein by reference.

In view of the non-planar configuration of the piperazine compounds in the compositions of the present invention and in view of the presence of a chiral center when X is other than hydrogen, the compounds exist in several isomeric forms. Thus, when X is hydrogen although there is no chiral center, the compound may be obtained in two isomeric forms as a result of restricted conformational mobility. When X is other than hydrogen, not only are there two isomeric forms as a result of restricted conformational mobility but there are also enantiomers possible for each of the isomeric forms. When R is cinnamoyl, cinnamyl, or substituted analogs thereof, there is also possible cis-trans isomerism. The isomer generally formed is the trans isomer. The compounds useful in the compositions and methods of the present invention include the various isomeric forms including mixtures of isomers in various proportions and when the compound is named without designation as to a specific isomer or to a racemic mixture or to a specific mixture of isomers, it is intended to be a generic designation embracing all isomers and mixtures of isomers.

The compounds of formula (I) both as enantiomers, as mixtures of enantiomers and other isomeric forms, and as acid addition salts are highly effective as inhibitors of calcium induced contraction of tracheal smooth muscle and/or vascular tissue. In particular, the compounds of the compositions of the present invention inhibit the contractile properties of smooth muscle and vascular tissues, and produce long lasting dilation of coronary vessels. The effect may be manifest in special vascular regions or in the entire vascular system. Thus, the compounds and the pharmaceutical compositions of the present invention may be used as vasodilators and are adapted to be employed in the treatment of cardiovascular diseases.

Pharmaceutical compositions of the present invention may contain varying amounts of the piperazine compound of Formula I or the salts thereof depending upon whether it is a concentrate composition or a treating composition, and if the latter, depending on the method of administration and further whether it is to be employed as a single dose or as multiple doses.

The present invention is also concerned with a method which comprises administering to subjects with cardiovascular disorders caused by high cellular concentration of calcium ion, a therapeutically effective amount of the piperazine compound of Formula I or a pharmaceutically acceptable acid addition salt thereof, or compositions containing said compounds.

The piperazine compounds in the compositions of the present invention which are free bases are solids, soluble in most inert organic solvents. The products of the present invention which are acid addition salts are crystalline solids.

The piperazine compounds of Formula I may be prepared by several routes. The preferred method for most of the compounds is a method which employs as the last step, a reaction between a halogen compound, preferably a chloro compound of the formula

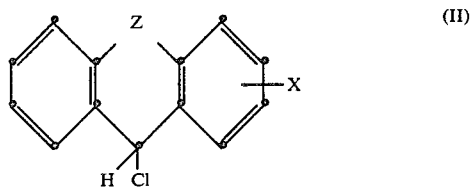

and a substituted piperazine compound

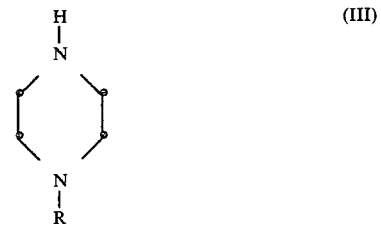

wherein R in said formula is other than hydrogen.

The reaction is generally carried out by mixing the reactants in solution in the presence of an acid binding agent at ambient temperature for time sufficient to complete the reaction with the formation of the desired product of Formula I and hydrogen chloride by-product. If the piperazine compound is readily available, a twofold molar excess or more of the piperazine compound may be employed, the excess piperazine compound acting as a binding agent for the hydrogen chloride by-product. Alternatively, a tertiary amine may be employed to serve this function. Suitable amines include triethylamine, diisopropylethylamine, pyridine and the like. Suitable solvents are nonpolar inert organic solvents such as dimethylformamide, dimethyl sulfoxide, tetramethylurea, 1,3-dimethyl-2-imidazolidinone, N,N-diethylacetamide, N,N-dimethylacetamide, N-ethylpyrrolidinone, and the like. The reaction is generally complete in several hours but conveniently may be allowed to proceed overnight.

After completion of the reaction, the product may be recovered by conventional procedures such as diluting the reaction mixture with water, extracting the desired product from the aqueous mixture with a water-immiscible organic solvent, such as diethyl ether, drying the organic solution and vaporizing the solvent to obtain the product as residue. The product may be purified by crystallization, recrystallization and/or chromatography. A useful purification procedure is Still or flash chromatography described in J. Org. Chem. 43, 292-3 (1978). The product also may be converted to an acid addition salt employing conventional procedures such as intimately admixing the base with an appropriate acid in a solvent such as ethanol and allowing the salt to separate from the solution. Salt formation may be employed as a method of obtaining purer crystalline product as well as for ultimate use as a salt. If salt formation is used as a means for isolation, the piperazine base product may be recovered from the salt by conventional procedures.

The reactant halo compounds are generally known; they may be prepared from precursor compounds as preliminary synthetic steps by well-known methods. In one general method, the reactant halo compound of Formula II may be prepared by reducing an appropriate ketone (IV) to a hydroxy compound (V) and thereafter converting the hydroxy compound to the reactant chloride (II) as seen in the following scheme:

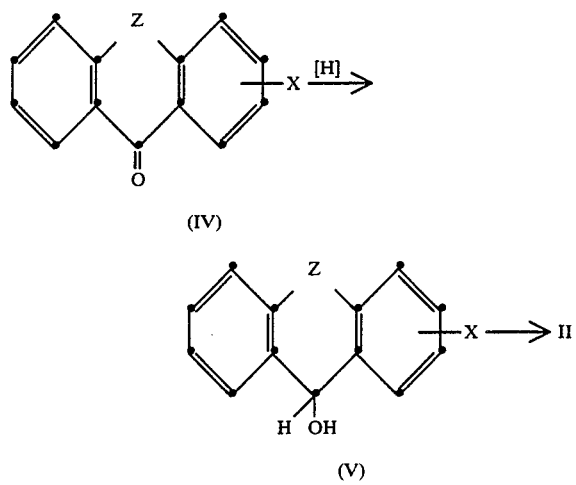

The ketone, which may be prepared by a well-established method first described by A. C. Cope et al., in J. Am. Chem. Soc., 73, 1673-8 (1951), is reduced to the corresponding hydroxy compound employing any suitable reducing method. Suitable reducing agents include sodium borohydride and lithium aluminum hydride. Conveniently it is carried out with sodium borohydride by adding dropwise an aqueous solution thereof in molar excess (about 2.5 molar excess) to a boiling alcohol (lower alkanol) solution of the ketone and thereafter heating at the reflux temperature until completion of the reaction with the formation of the corresponding hydroxy. Alternatively, the ketone and sodium borohydride may be stirred together in alcohol made slightly basic with addition of alkali at ambient temperature. The hydroxy compound may be recovered by conventional procedures, e.g. vaporizing the solvent, washing the residue, filtering and drying may be employed for the preparation of the chloro compound without further purification.

In preparing the chloro compound, the dried alcohol compound is dissolved in an inert organic solvent such as benzene or toluene and caused to react with a halogenating agent, preferably thionyl chloride but also thionyl bromide, a phosphorus halide or oxyhalide or a hydrohalic acid. A convenient procedure is to mix together the appropriate hydroxy compound, excess thionyl chloride and benzene and heat at reflux temperature from about one to three hours. Thereafter, the solvent and unreacted thionyl chloride are coevaporated at reduced pressure leaving the chloro compound as residue. Generally, fresh solvent is added to the residue and the coevaporation repeated several times to obtain the Formula II halo compound in sufficient purity to employ in the reaction with the piperazine compound.

As is also apparent, if the intermediate hydroxy compound is available, the synthesis may be initiated from the hydroxy compound.

The reactant piperazine compound of Formula III is frequently readily available. In the case of compounds where the piperazine compound is not readily available it may be prepared by reacting unsubstituted piperazine with an R-halogen compound such as RCl as follows:

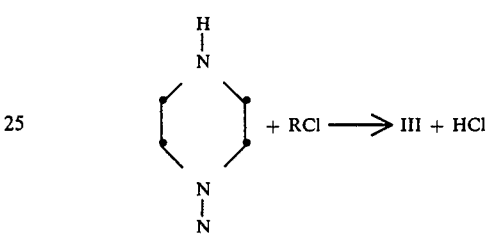

RCl may be an alkyl halide, halohydrin or an acyl halide depending on the nature of the R group. The reaction may be carried out by mixing piperazine and RCl preferably in the presence of a tertiary amine in an inert solvent at ambient temperature for up to several hours and thereafter recovering the substituted piperazine by conventional procedures.

When R in Formula I is aralkenyl, i.e., cinnamyl or substituted cinnamyl, it is preferably prepared by the following sequence of reactions:

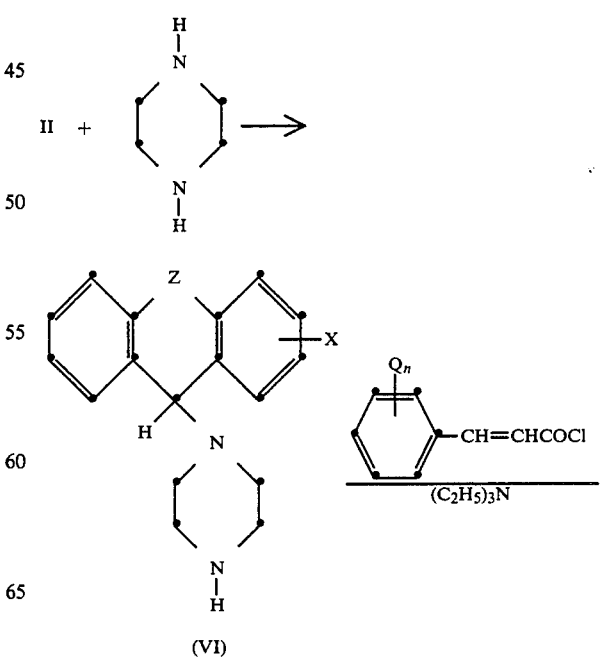

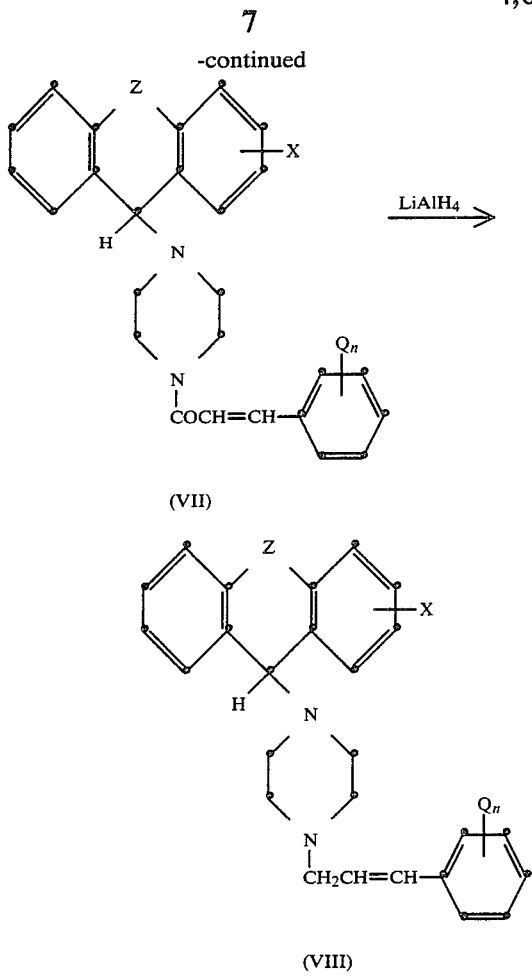

(VII)

(VIII)

According to the sequence of reactions, the chloro compound of Formula II is reacted first with piperazine to produce a piperazine compound of Formula VI. The latter is then reacted with aralkenoyl chloride, i.e., cinnamoyl or lower alkoxycinnamoyl chloride

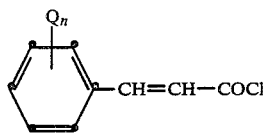

wherein Q is lower alkoxy and n is 0 to 3 to obtain a aralkenoyl compound (VII) which then may be reduced to the aralkenyl compound (VIII).

The first step in the foregoing sequence of reactions may be carried out by mixing the reactants in solution in the presence of excess piperazine at ambient temperature in a manner similar to that previously described for the reaction between the halo compound and the substituted piperazine compound (III). After completion of the reaction, the product may be recovered by conventional procedures.

The second step of the reaction may be carried out by adding the aralkenoyl halide to a stirred mixture of piperazine compound VI, and a tertiary-organic base, and continuing the mixing for from about 0.5 to several hours at room temperature to obtain an aralkenoylpiperazine compound VII in the reaction mixture. For the reaction, the piperazine compound VI and aralkenoyl halide are employed in substantially equimolar proportions. The reaction is carried out in the presence of two- to fourfold molar excess of a tertiary amine to bind the hydrogen halide by-product which is formed. Suitable amines include triethylamine, trimethylamine, diisopropylethylamine, tripropylamine, pyridine, collidine and the like. A solvent is employed in the reaction. Suitable solvents include methylene chloride, chloroform, carbon tetrachloride and the like. The aralkenoyl piperazine VII may be recovered from the reaction mixture by diluting the mixture with an inert solvent such as ether, washing the ethereal solution with appropriate aqueous reagents such as dilute hydrochloric acid, bicarbonate and brine, drying, and then vaporizing the solvent.

The aralkenoyl piperazine compound (VII) then is reacted with a reducing agent to obtain the desired product VIII. Lithium aluminum hydride is a convenient and suitable reagent although other reducing agents may be employed. When employing lithium aluminum hydride, the reaction is carried out in a solvent in an inert atmosphere. Suitable solvents are ethereal solvents, preferably tetrahydrofuran but also diethyl ether, diisopropyl ether, dioxane, and the like. Argon or nitrogen atmosphere is provided. Generally from about 1.5 to 2.5 molar excess of the lithium aluminum hydride is employed. Lithium aluminum hydride in solid form may be added in small portions to a solution of the aralkenoylpiperazine in ethereal solution. Alternatively, a solution of the aralkenoylpiperazine may be contacted with a solution of the reducing agent. The addition is carried out at ambient temperature. After completion of the addition, the resulting mixture is stirred for time sufficient to complete the reaction. The entire operation may be carried out at ambient temperature or may be heated to the reflux temperature of the solution to complete the reaction. Usually the stirring is carried out for from several hours to conveniently overnight. After completion of the reaction, the mixture may be diluted with solvent and the reaction quenched employing the "n, n, 3n" method, the lithium and aluminum hydroxide by-products filtered the filtrate dried, the drying agent filtered, the solvent vaporized and the product recovered as residue. The latter may be purified by conventional procedures, including chromotographic adsorption methods or may be converted into a salt.

The "n,n,3n" method for quenching the reaction is described on page 584 of Fieser and Fieser, "Reagents for Organic Synthesis" John Wiley and Sons, Inc., New York, 1067. Briefly it entails treating the stirred reduction mixture from n grams of lithium aluminum hydride by successive dropwise addition of n milliliters of water, n milliliters of 15 percent sodium hydroxide and 3n milliliters of water producing a granular precipitate of hydroxides which can be readily filtered and washed.

The acid addition salts of Formula I which are also within the scope of active agents in the methods and compositions of the present invention may be obtained by reacting the compounds of Formula I with the appropriate inorganic or organic acid and isolating the salt by conventional procedures.

The usefulness of the compounds in the compositions of the present invention as calcium entry blockers may be demonstrated by the ability of the compounds to inhibit calcium induced contraction of tracheal smooth muscle or of vascular tissue. The property may be observed in a test in which segments of vascular smooth muscle obtained from male Sprague-Dawley rats are suspended in physiological salt solution in a tissue bath instrumented for recording contractions. After the tissue has been equilibrated, washed in calcium-free physiological salt solution and then depolarized, 1.0 mM calcium chloride is re-added to induce contraction. After the contraction has reached a plateau, tissues are washed and a test compound or vehicle is added to determine the effect achieved by the above cyclic protocol on a second contraction. From measuring the initial contraction as well as the second contraction in the presence of the test compound, the extent of inhibition may be calculated. The results of these tests for representative compounds in the compositions of the present invention are seen in the following table. The table lists representative compounds showing at least 25% inhibition when tested at very low concentrations of $10^{-7}$M or less. With less preferred compounds such as those having a cyclooctene ring instead of cycloheptene ring or having less preferred substituents on the ring such as an alkylsulfonyl group, comparable results may be obtained by employing concentrations higher than $10^{-7}$M.

| Active Component | Percent Inhibition of Rat Aorta |
|---|---|
| 1-Cinnamyl-4-(5H—dibenzo[a,d]cyclohepten-5-yl)piperazine | 89% at $10^{-8}$ M |
| 1-(3-Bromo-5H—dibenzo[a,d]cyclohepten-5-yl)-4-methylpiperazine | 48% at $10^{-8}$ M |
| 1-(3-Chloro-5H—dibenzo[a,d]cyclohepten-5-yl)-4-methylpiperazine | 90% at $10^{-7}$ M |
| 1-Methyl-4-(3-methylthio-5H—dibenzo[a,d]-cyclohepten-5-yl)piperazine | 76% at $10^{-7}$ M |
| 1-(3-Methoxy-5H—dibenzo[a,d]cyclohepten-5-yl)-4-methylpiperazine | 65% at $10^{-7}$ M |
| 1-(5H—Dibenzo[a,d]cyclohepten-5-yl)-4-methylpiperazine | 59% at $10^{-7}$ M |
| 1-(3-Bromo-5H—dibenzo[a,d]cyclohepten-5-yl)-4-cinnamylpiperazine | 41% at $10^{-7}$ M |
| 1-(10,11-Dihydro-3-methoxy-5H—dibenzo[a,d]cyclohepten-5-yl)-4-methylpiperazine | 36% at $10^{-7}$ M |
| 1-(5H—Dibenzo[a,d]cyclohepten-5-yl)piperazine | 34% at $10^{-7}$ M |
| 1-(6,11-Dihydrodibenzo[b,c]thiepin-11-yl)-4-methylpiperazine | 30% at $10^{-7}$ M |
| Ethyl 4-(5H—dibenzo[a,d]cyclohepten-5-yl)-1-piperazinecarboxylate | 37% at $10^{-7}$ M |

The process of the present invention comprises administering to subjects with cardiovascular disorders caused by high cellular concentrations of calcium ion, a therapeutically effective amount of a piperazine compound of Formula I or a pharmaceutically acceptable acid addition salt thereof, or compositions containing said compounds. In general, the daily dose may be that sufficient to provide between about 0.3 and 40 mg/kg/day, preferably, in the range 1.0 and 12 mg/kg/day while considering patients' health, weight, age, and other factors which influence response to a drug as well as the particular drug to be employed. Further, since the drug is useful in several aspects of cardiovascular therapy, the dose is also dependent on the particular disease to be alleviated. The drug may be administered orally or parenterally or by any other means, and in a single unit or in a number of smaller units given during the period of a day in compositions hereinafter detailed.

The pharmaceutical compositions useful for the process of the present invention comprises a piperazine compound of Formula I or a pharmaceutically acceptable acid addition salt thereof in intimate admixture with a pharmaceutically acceptable carrier. To prepare the pharmaceutical compositions of this invention, a compound of Formula (I) or acid addition salt thereof, as the active ingredient, is intimately admixed with a pharmaceutical carrier according to conventional pharmaceutical compounding techniques. The carrier may take a wide variety of forms depending on the form of preparation desired for administration, e.g., oral or parenteral. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, may be included for purposes such as for example, aiding solubility or for preservation. When the parenteral is an injectable suspension, the liquid carrier may include agents such as suspending agents.

It is especially advantageous to formulate the pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the therapeutic effect in association with the required pharmaceutical carrier. Examples of such dosage unit forms are tablets, capsules, pills, powder packets, wafers, teaspoonsful, tablespoonsful, and the like, and segregated multiples thereof. The amount of active ingredient per dosage unit will be from about 0.075 mg. to about 10 mg. Preferably, the amount of active ingredient will be from about 0.3 to about 4 mg.

The following examples illustrate the invention but are not to be construed as limiting.

Examples I–XVIII illustrate the preparation of the compounds for the compositions and methods of the present invention.

EXAMPLE I 1-(5H-Dibenzo[a,d]cyclohepten-5-yl)piperazine

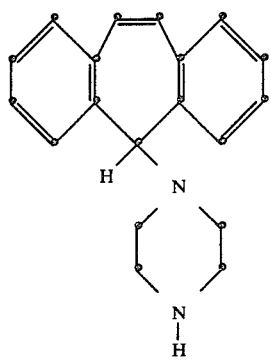

5.00 grams (24 millimoles) of 5H-dibenzo[a,d]cyclohepten-5-ol and 8.57 grams (72 millimoles) of thionyl chloride were heated together in refluxing benzene for 0.5 hour, then the solvent was vaporized to obtain a 5-chloro-5H-dibenzo[a,d]cycloheptene intermediate as residue.

The chlorodibenzocycloheptene intermediate thus prepared was dissolved in 50 milliliters of chloroform, the solution added dropwise to a solution of 41.3 grams (480 millimoles) of piperazine in 150 milliliters of chloroform and the resulting mixture stirred for two days. At the end of this time, the mixture was washed successively with 20 percent sodium hydroxide, water, and brine, then dried over potassium carbonate. The drying agent was filtered off and the solvent vaporized to obtain 6.70 grams (100 percent yield) of 4-(5H-dibenzo[a,d]cyclohepten-5-yl)piperazine product as residue. A portion of the product was recrystallized from acetonitrile to obtain a purified product, m.p. 139°-141° C. Elemental analyses of the product after drying for 24 hours at 65° C. at 20 millimeters of mercury pressure were as follows:

Calc'd for $C_{19}H_{20}N_2$; C, 82.57; H, 7.29; N, 10.14. Found C, 82.61; H, 7.36; N, 10.12.

EXAMPLE II

1-Cinnamoyl-4-(5H-dibenzo[a,d]cyclohepten-5-yl)piperazine and
1-cinnamyl-4-(5H-dibenzo[a,d]cyclohepten-5-yl)piperazine

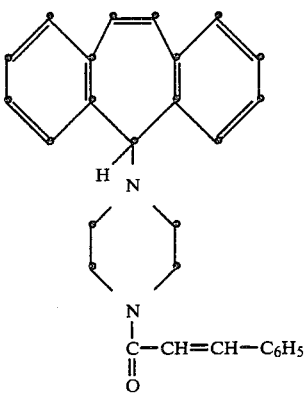

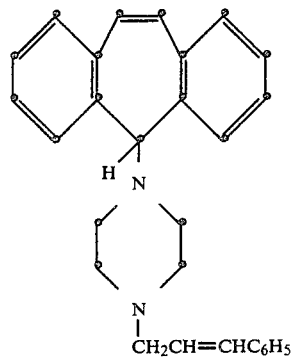

Preparation of 4-(5H-dibenzo[a,d]cyclohepten-5-yl)-1-cinnamoylpiperazine intermediate 4.05 grams (40.0 millimoles) of triethylamine was added to 5.50 grams (19.9 millimoles) of 4-(5H-dibenzo[a,d]cyclohepten-5-yl)piperazine in 50 milliliters of dry methylene chloride and the mixture was cooled to 0° C. A solution of 3.31 grams (19.9 millimoles) of cinnamoyl chloride was added dropwise over a 1.5 hour period. When the addition was complete, the mixture was stirred an additional one hour at about 0° C. and then washed successively with 20 percent aqueous sodium hydroxide and then with brine. The washed solution was dried over magnesium sulfate, the magnesium sulfate filtered off and the solvent evaporated in vacuo to obtain 6.70 grams (83 percent yield) of the 4-(5H-dibenzo[a,d]cyclohepten-5-yl)-4-cinnamoylpiperazine.

Preparation of 4-(5H-dibenzo[a,d]cyclohepten-5-yl)-1-cinnamylpiperazine 1.25 grams (33.0 millimoles) of solid lithium aluminum hydride was added portionwise with stirring in an argon atmosphere over a 5 minute period to a solution of 6.70 grams of the 4-(5H-dibenzo[a,d]cyclohepten-5-yl)-4-cinnamoylpiperazine in 100 milliliters of dry tetrahydrofuran. After completion of the addition, the mixture was stirred at room temperature for 15 hours, refluxed for one-half hour, then cooled to room temperature and quenched by the n,n,3n method. The filtrate after filtration and removal of lithium and aluminum hydroxides was dried over magnesium sulfate, the drying agent filtered off and the solvent vaporized in vacuo to obtain a foam residue which was purified by chromatographing on a silica gel column to obtain a fraction which after crystallization from ethyl acetate had a melting point of 112°-115° C. NMR spectra indicated the product to be the trans isomer. Elemental analyses were as follows:

Calc'd for $C_{28}H_{28}N_2$: C, 85.67; H, 7.19; N, 7.15. Found C, 85.31; H, 7.47; N, 6.94.

EXAMPLE III 1-(3-Bromo-5H-dibenzo[a,d]cyclohepten-5-yl)-4-cinnamoylpiperazine and 1-(3-bromo-5H-dibenzo[a,d]cyclohepten-5-yl)-4-cinnamylpiperazine and its hydrogen oxalate salt

Preparation of 1-(3-bromo-5H-dibenzo[a,d]cyclohepten-5-yl)-4-cinnamoylpiperazine 663 milligrams (2.31 millimoles) of 3-bromo-5H-dibenzo[a,d]cyclohepten-5-ol, 825 milligrams (6.94 millimoles) of thionyl chloride and 10 milliliters of benzene were mixed together and refluxed for 1.5 hours and the solvent removed in vacuo to obtain a 3-bromo-5-chloro-5H-dibenzo[a,d]-cycloheptene product as residue. The residue was dissolved in 10 milliliters of dimethylformamide and 1.74 milliliters (1.29 grams, 10.0 millimoles) of ethyl diisopropyl amine and 500 milligrams (2.31 millimoles) of cinnamoylpiperazine added thereto and the resulting mixture stirred overnight to obtain a 1-(3-bromo-5H-dibenzo[a,d]cyclohepten-5-yl)-4-cinnamoylpiperazine compound in the reaction mixture. It was recovered as residue by vaporizing the solvent in vacuo, the residue then was dissolved in ethyl acetate, the ethyl acetate solution washed with three 50 milliliter portions of water and with one 100 milliliter portion of brine, and then dried over potassium carbonate. After removing the drying agent, the solvent was evaporated in vacuo from the dried solution to obtain 1.07 grams (95 percent yield) of the cinnamoylpiperazine compound.

Preparation of 1-(3-bromo-5H-dibenzo[a,d]cyclohepten-5-yl)-4-cinnamylpiperazine 167 milligrams (4.41 millimoles) of lithium aluminum hydride was added with stirring under argon atmosphere to a solution of 1070 milligrams (2.20 millimoles) of the cinnamoylpiperazine prepared as above described in 10 milliliters of dry tetrahydrofuran. The mixture was stirred for about an hour, then a sample subjected to thin layer chromatographic analysis which indicated consumption of the starting material. The reaction was quenched employing the n,n,3n procedure and the reaction mixture dried over magnesium sulfate. Thereafter the mixture was filtered to obtain the dried solution, and the solvent vaporized in vacuo to obtain a yellow foamy solid which was flash chromatographed on silica gel with 25/75 ethyl acetate/hexane mixture to obtain the desired 1-(3-bromo-5H-dibenzo[a,d]cyclohepten-5-yl)-4-cinnamylpiperazine compound as a white foamy solid. A 267 milligram portion of the solid was dissolved in 3 milliliters of absolute ethanol and 1 milliliter of chloroform, and mixed with a solution of 71 milligrams (0.566 mole) of oxalic acid dihydrate in 1 milliliter of absolute ethanol, and thereafter placed in a freezer overnight whereupon some crystals separated. The crystals were removed and the mother liquor concentrated to obtain a residue which was redissolved in methanol. The methanol was slowly evaporated from the solution to obtain crystals which after grinding and drying in vacuo at 100° C. for 24 hours amounted to 274.4 milligrams of a product, m.p. dec. at 120° C., which was determined by elemental analyses to be 1-(3-bromo-5H-dibenzo[a,d]cyclohepten-5-yl)-4-cinnamylpiperazine hydrogen oxalate monohydrate. Elemental analyses were as follows:

Calc'd for $C_{30}H_{31}BrN_2O_5$: C, 62.18; H, 5.39; N, 4.83. Found: C, 62.35; H, 5.51; N, N, 57.

EXAMPLE IV 1-(3-Bromo-5H-dibenzo[a,d]cyclohepten-5-yl)-4-methylpiperazine

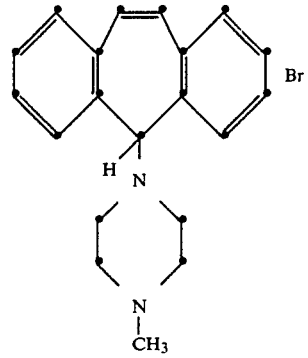

1.00 gram (3.27 millimoles) of 3-bromo-5-chloro-5H-dibenzo[a,d]cycloheptene, 0.7 gram (about 7 millimoles) of N-methylpiperazine and 3 milliliters of dimethylformamide were stirred together at room temperature under an atmosphere of nitrogen for 60 hours. At the end of this period, water and aqueous sodium carbonate solution was added, and the resulting aqueous solution extracted with ether. The ether solution was washed five times with water, then with saturated sodium chloride solution and dried over magnesium sulfate. The solvent was removed from the dried solution in vacuo to obtain a residue. The residue was triturated with acetonitrile and crystallized from acetonitrile. It was then purified by passing through a Still column using 3 percent methanol in chloroform as eluant, crystallized from acetonitrile, and the crystals dried over phosphorus pentoxide at 78° C./0.2 mm Hg for 17 hours to obtain 0.57 gram of 1-(3-bromo-5H-dibenzo[a,d]cyclohepten-5-yl)-4-methylpiperazine product, m.p. 128°–130° C. Elemental analyses were as follows:

Calc'd for $C_{20}H_{21}BrN_2$: C, 65.04; H, 5.73; N, 7.59. Found: C, 65.00; H, 5.89; N, 7.55.

EXAMPLE V 1-(3-Chloro-5H-dibenzo[a,d]cyclohepten-5-yl)-4-methylpiperazine

A solution of 0.30 gram (0.0078 mole) of sodium borohydride in 5 milliliters of water was added to a solution of 0.75 gram (3.2 millimoles) of 3-chloro-5H-dibenzo[a,d]cyclohepten-5-one in 50 milliliters of methanol and the resulting mixture heated for 15 minutes at reflux temperature to obtain 3-chloro-5H-dibenzo[a,d]cyclohepten-5-ol intermediate in the reaction mixture. The solvent was evaporated and the residue intermediate slurried with water, filtered, washed and dried at 65° C. in vacuum oven for three hours.

The thus dried 3-chloro-5H-dibenzo[a,d]cyclohepten-5-ol intermediate was mixed with 10 milliliters of benzene and 10 milliliters of thionyl chloride and the resulting mixture stirred at reflux temperature for 2 hours to obtain 3,5-dichloro-5H-dibenzo[a,d]cycloheptene intermediate in the reaction mixture. The mixture was cooled and evaporated under reduced pressure to recover the chloro intermediate as residue.

3 milliliters of N-methylpiperazine and 3 milliliters of dimethylformamide was added to the residue and the resulting mixture stirred overnight at room temperature. At the end of this period, the reaction mixture was diluted with 200 milliliters of water and extracted with three 75 milliliter portions of ether. The ether solutions were combined, washed with three 75 milliliter portions of water, dried, filtered and the solvent evaporated in vacuo to obtain the desired 1-(3-chloro-5H-dibenzo[a,d]cyclohepten-5-yl)-4-methyl-piperazine products as residue. The product after crystallization from acetonitrile and drying over phosphorous pentoxide at 78° C./0.1 millimeter of mercury pressure for 12 hours had a melting point of 145°–146° C. Elemental analyses were as follows:

Calculated for $C_{20}H_{21}N_2Cl$: C, 73.94; H, 6.52; N, 8.63; Cl, 10.91. Found: C, 73.82; H, 6.72; N, 8.45.

EXAMPLE VI 1-(3-Methoxy-5H-dibenzo[a,d]cyclohepten-5-yl)-4-methylpiperazine

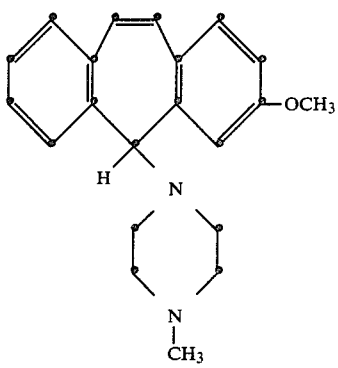

0.7 gram (0.018 mole) of sodium borohydride was added to a solution of 1.5 grams (6.5 millimoles) of 3-methoxy-5H-dibenzo[a,d]cyclohepten-5-one in 30 milliliters of ethanol to which 1 drop of 40 percent sodium hydroxide had been added and the resulting mixture was stirred overnight at room temperature. At the end of this time, water was added and the mixture subjected to reduced pressure to remove the ethanol. The remaining aqueous solution was extracted with ether, the ether solution washed successively with water, dilute sodium hydroxide, water and saturated sodium chloride and then dried over magnesium sulfate. The sulfate was filtered and the dried solution subjected to reduced pressure to vaporize the solvent and obtain a residue which was further dried by repeated additions of benzene followed by vaporization to dryness under reduced pressure to recover the 3-methoxy-5H-dibenzo[a,d]cyclohepten-5-ol intermediate as a white solid.

The cycloheptenol intermediate thus obtained was dissolved in 40 milliliters of benzene, 5 milliliters of thionyl chloride added to the resulting solution and the mixture heated at reflux temperature for 1.5 hours. Thereafter, the mixture was cooled and subjected to reduced pressure to obtain the 5-chloro-3-methoxy-5H-dibenzo[a,d]cycloheptene intermediate (chloro compound). The chloro compound was purified by repeatedly dissolving in benzene and concentrating to dryness under reduced pressure to co-evaporate the benzene and thionyl chloride.

To a solution of the purified chloro compound dissolved in 10 milliliters of dimethylformamide was added a solution of 2 grams (about 20 millimoles) of 1-methylpiperazine in 5 milliliters of dimethylformamide and the resulting mixture allowed to stand overnight at room temperature. The mixture was subjected to reduced pressure to remove most of the dimethylformamide, then washed with a large amount of aqueous bicarbonate. The aqueous mixture was extracted twice with diethyl ether. The ether solutions were combined and washed five times with water, then with saturated sodium hydroxide and dried over magnesium sulfate. The dried solution was subjected to reduced pressure to recover the desired 1-(3-methoxy-5H-dibenzo[a,d]cyclohepten-5-yl)-1-methylpiperazine product as residue. The product was purified by adding acetonitrile, vaporizing in vacuo to dryness, then recrystallizing from acetonitrile to obtain 1.06 grams of purified product, m.p. 118°–118.5° C. Elemental analyses for the product were as follows:

Calc'd for $C_{21}H_{24}N_2O$: C, 78.17; H, 7.55; N, 8.75. Found C, 78.62; H, 7.74; N, 8.61.

EXAMPLE VII

1-Methyl-4-(3-methylthio-5H-dibenzo[a,d]cyclohepten-5-yl)piperazine

In operations carried out in a manner similar to that described in Example VI, 0.5 gram (13 millimoles) of sodium borohydride was added to a solution of 0.8 gram (3.2 millimoles) of 3-methylthio-5H-dibenzo[a,d]cyclohepten-5-one in 20 milliliters of ethanol to which 1 drop of 40 percent sodium hydroxide had been added and the resulting mixture stirred overnight at room temperature. Thereafter, water was added to the reaction mixture, the aqueous mixture subjected to reduced pressure to remove the ethanol, the remaining aqueous solution extracted with ether, the ether solution washed successively with water and saturated sodium chloride, and then dried over magnesium sulfate. The dried solution was subjected to reduced pressure to obtain the 3-methylthio-5H-dibenzo[a,d]cyclohepten-5-ol intermediate as a white solid.

Molar excess (5 milliliters) of thionyl chloride was added to a solution of the 3-methylthio-5H-dibenzo[a,d]cyclohepten-5-ol intermediate in 45 milliliters of benzene and the resulting mixture heated under reflux for two hours to obtain a 5-chloro-3-methylthio-5H-dibenzo[a,d]cycloheptene (chloro compound) intermediate in the reaction mixture. The reaction mixture was subjected to reduced pressure to co-evaporate benzene and unreacted thionyl chloride, and the procedure repeated with several additions of benzene to obtain a purified chloro compound intermediate.

A solution of 0.7 gram (7 millimoles) of N-methylpiperazine in 10 milliliters of dimethylformamide was added to the chloro compound thus prepared and the resulting mixture stirred overnight at room temperature to obtain a product in the reaction mixture. The product was recovered by concentrating the mixture in vacuo, adding aqueous bicarbonate to the concentrate extracting the resulting aqueous solution with ether, washing the ether solution with water and saturated sodium chloride solution, drying over magnesium sulfate, filtering and then subjecting the filtrate to reduced pressure to obtain the desired 1-methyl(-4-(3-methylthio-5H-dibenzo[a,d]cyclohepten-5-yl)piperazine product as residue. The latter was purified by twice dissolving in and concentrating from acetonitrile and thereafter crystallizing from acetonitrile to obtain a purified product, m.p. 113°–114° C. Elemental analyses for the product were as follows:

Calc'd for $C_{21}H_{24}N_2S$: C, 74.95; H, 7.9; N, 8.33. Found: C, 75.29; H, 7.54; N, 8.26.

EXAMPLE VIII

1-Methyl-4-(3-(methylsulfonyl)-5H-dibenzo[a,d]-cyclohepten-5-yl)piperazine

A solution of 1.33 grams (35 millimoles) of sodium borohydride in 5 milliliters of water was added dropwise to a boiling stirred solution of 4.00 grams (0.0141 mole) of 3-methylsulfonyl-5H-dibenzo[a,d]cyclohepten-5-one in 100 milliliters of ethanol. The reaction mixture was stirred under reflux for one hour, then cooled and subjected to reduced pressure to vaporize the solvent and to obtain a residue. The residue was crystallized from methanol; the crystals after drying under reduced pressure at about 65° C. and amounted to 3.10 grams of 3-methylsulfonyl-5H-dibenzo[a,d]cyclohepten-5-ol intermediate.

The cycloheptenol intermediate thus obtained was mixed together with 20 milliliters of benzene and 20 milliliters of thionyl chloride and stirred at reflux temperature for 3 hours and the resulting mixture evaporated to dryness. Toluene was added to the residue and the unreacted thionyl chloride and toluene co-evaporated whereupon crystals of 5-chloro-3-methyl-sulfonyl-5H-dibenzo[a,d]cycloheptene intermediate formed.

25 milliliters of dimethylformamide and 10 milliliters of 1-methylpiperazine were added to the intermediate chloro compound thus obtained, and the resulting mixture stirred at room temperature for three hours. At the end of this period, the reaction mixture was poured into 500 milliliters of water and the resulting aqueous mixture was extracted three times with chloroform. The chloroform solutions were combined and the solvent vaporized in vacuo to obtain crude 1-methyl-4-(3-(methylsulfonyl)-5H-dibenzo[a,d]-cyclohepten-5-yl)piperazine product as residue. The product was triturated with ether and filtered to obtain white crystals which after recrystallization from acetonitrile and drying at 78° C./0.1 mm Hg over phosphorus pentoxide for 18 hours has a melting point of 123° C. The elemental analyses of the product were as follows:

Calcd for $C_{21}H_{24}N_2O_2S$: C, 68.45; H, 6.57; N, 7.60. Found C, 68.43; H, 6.91, N, 7.61.

EXAMPLE IX 1-(3-Chloro-11-bromo-5H-dibenzo[a,d]cyclohepten-5-yl)-4-methylpiperazine

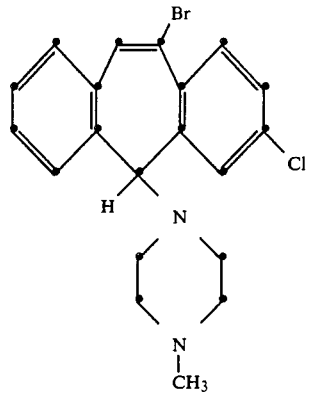

In a similar manner, a solution of 1.7 grams of sodium borohydride in 20 milliliters of water was added dropwise to a solution of 3-chloro-11-bromo-5H-dibenzo[a,d]cyclohepten-5-one in 100 milliliters of boiling methanol and the resulting mixture refluxed for 1.5 hours to obtain a 3-chloro-11-bromo-5H-dibenzo[a,d]cyclohepten-5-ol intermediate which was recovered by evaporating the mixture to dryness in vacuo, then washing with water, filtering and drying under reduced pressure at about 60° C.

The cycloheptenol intermediate thus obtained was mixed together with 25 milliliters of benzene and 25 milliliters of thionyl chloride and the resulting mixture stirred while refluxing for 2 hours. Thereafter, the solvent and thionyl chloride were evaporated under reduced pressure. 50 milliliters of benzene was added and the added solvent and thionyl chloride co-evaporated; the procedure was repeated four more times to obtain a 3-chloro-11-bromo-2H-dibenzo[a,d]cycloheptene intermediate as residue.

The chloro intermediate compound thus obtained was mixed together with 3.51 grams (millimoles) of 1-methylpiperazine and 25 milliliters of dimethylformamide and the mixture stirred at room temperature overnight to obtain the desired 1-(3-chloro-11-bromo-5H-dibenzo[a,d]cyclohepten-5-yl)-4-methylpiperazine compound. The product was recovered by pouring the reaction mixture into water, extracting with ether several times, washing the ether extract, drying over magnesium sulfate, filtering, and evaporating the solvent to obtain a residue which after triturating with ether became crystalline. The product after recrystallization from acetonitrile had a melting point of 148°–150° C. Elemental analyses were as follows:

Calc'd for $C_{20}H_{20}BrClN$: C, 59.49; H, 5.00; N, 6.94. Found C, 59.75; H, 5.09; N, 6.88.

EXAMPLE X 1-(11-Chloro-5,10-dihydrodibenzo[a,d]cycloocten-5-yl)-4-methylpiperazine and hydrogen maleate salt

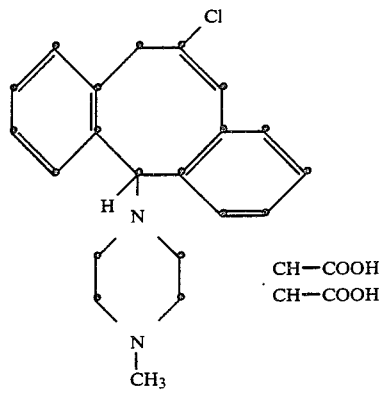

In a similar manner to that described in the preceeding examples, a solution of 2.23 grams (59 millimoles) of sodium borohydride in 25 milliliters of water was added dropwise to a boiling solution of 6.0 grams (24 millimoles) of 11-chloro-5,10-dihydrodibenzo[a,d]cyclooct-en-5-one in 100 milliliters of methanol and the resulting mixture heated at reflux temperature for one hour. The mixture was then allowed to cool, subjected to reduced pressure to evaporate most of the methanol and to recover an oily residue. The residue was partitioned between water and toluene and the aqueous portion extracted twice with toluene. The toluene solutions were combined and washed with water, dried over magnesium sulfate, filtered, and the dried solution subjected to reduced pressure to evaporate the solvent and to obtain a 11-chloro-5,10-dihydrodibenzo[a,d]cyclooctene-5-ol intermediate as solid residue. The cyclooctenol intermediate was dried overnight at 60° C. and reduced pressure for use in the next step.

30 milliliters of thionyl chloride was added to the solid obtained as above described and the resulting mixture stirred at reflux temperature for 1.5 hours. Thereafter, most of the unreacted thionyl chloride was evaporated in vacuo, benzene added to the residue, and the benzene and thionyl chloride co-evaporated until the residue became crystallized with the formation of crystalline 5,11-dichloro-5,10-dihydrodibenzo[a,d]cyclooctene intermediate.

5.0 grams (50 millimoles) of N-methylpiperazine and 25 milliliters of dimethylformamide were added to the residue and the mixture stirred at room temperature overnight. Thereafter, the reaction mixture was poured into 500 milliliters of water, the aqueous mixture extracted with four 100 milliliter portions of diethyl ether, the ether solutions combined and washed with water and then dried over magnesium sulfate. The dried solution (after removal of drying agent) was evaporated and triturated with acetonitrile. The solvent was evaporated and the 1-(11-chloro-5,10-dihydrodibenzo[a,d]cyclooct-en-5-yl)-4-methylpiperazine product obtained. The product was mixed with 2.08 grams (0.017 mole) of maleic acid and ethanol-ether to obtain the crystalline maleate salt of the piperazine product. The product after recrystallization from hot isopropanol had a melting point of 148°–152° C. Elemental analyses were as follows:

Calc'd for $C_{21}H_{23}ClN_2 \cdot C_4H_4O_4$: C, 66.00; H, 5.98; N, 6.16. Found C, 65.63; H, 6.11; N, 5.80.

EXAMPLE XI 1-(10,11-Difluoro-5H-dibenzo[a,d]cyclohepten-5-yl)-4-methylpiperazine and hydrogen maleate salt

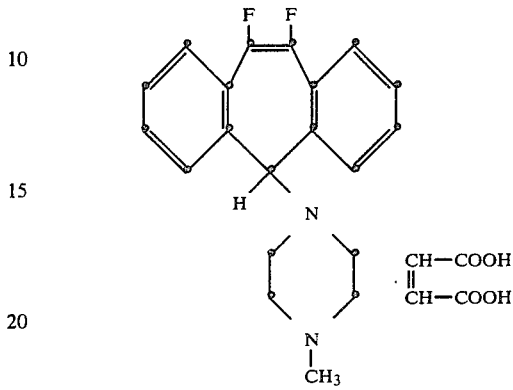

In a similar manner, a solution of 0.20 gram (52 millimoles) of sodium borohydride in 5 milliliters of water was added dropwise with stirring to a boiling refluxing solution of 0.50 gram (21 millimoles) of 10,11-difluoro-5H-dibenzo[a,d]cyclohepten-5-one in 50 milliliters of methanol; the stirring and refluxing were continued for one hour, and the mixture thereafter allowed to cool. Most of methanol then was vaporized from the mixture, water added and stirred to obtain white crystalline 10,11-difluoro-5H-dibenzo[a,d]cyclohepten-5-ol intermediate. The latter was washed with water and dried under reduced pressure at about 75° C.

The alcohol intermediate thus obtained was mixed with 10 milliliters of benzene and 10 milliliters of thionyl chloride and the resulting mixture stirred at reflux temperature for 1.5 hours to obtain 5-chloro-10,11-difluoro-5H-dibenzo[a,d]cycloheptene in the reaction mixture. The mixture was subjected to reduce pressure to vaporize unreacted thionyl chloride, and to recover the chloro intermediate as residue.

The chloro intermediate was dissolved in 5 milliliters of dimethylformamide, 5 milliliters of 1-methylpiperazine added thereto and the resulting mixture stirred overnight at room temperature to obtain a 1-(10,11-difluoro-5H-dibenzo[a,d]cyclohepten-5-yl)-4-methylpiperazine product in the reaction mixture. The product was recovered from the reaction mixture by vaporizing the unreacted piperazine and solvent in vacuo at 50°–60° C., adding 300 milliliters of water to the residue and extracting the aqueous solution with four 75 milliliters portions of diethyl ether, washing the combined ether solution several times with water, drying the solution over magnesium sulfate, filtering the drying agent and evaporating the filtrate, in vacuo to obtain the product as an oily residue. To the residue was added 0.24 gram (21 millimoles) of maleic acid in 5 milliliters of ethanol and the mixture heated and filtered while hot to obtain 1-(10,11-difluoro-5H-dibenzo[a,d]cyclohepten-5-yl)-4-methylpiperazine hydrogen maleate salt product which crystallized as needles. The crystals, after washing with ethanol and drying had a melting point of 193°–195° C. Elemental analyses were as follows:

Calc'd for $C_{20}H_{20}F_2N_2 \cdot C_4H_4O_4$: C, 65.15; H, 5.47; N, 6.33. Found C, 65.25; H, 5.79; N, 6.27.

EXAMPLE XII 1-(6,11-Dihydrodibenzo[b,e]thiepin-11-yl)-4-methylpiperazine and hydrogen maleate salt

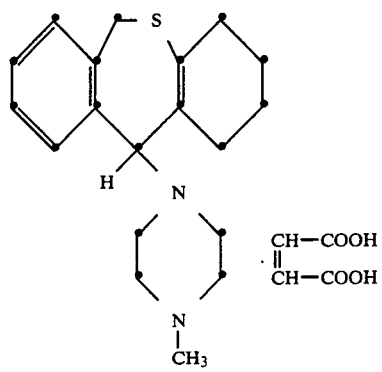

In a similar manner, 0.5 gram (13 millimoles) of sodium borohydride was added to a solution of 2.26 grams (13 millimoles) of 6,11-dihydrodibenzo[b,e]thiepin-11-one in 50 milliliters of ethanol to which a few drops of 40 percent sodium hydroxide had been added and the mixture stirred at room temperature overnight to obtain 6,11-dihydrodibenzo[b,e]thiepin-11-ol intermediate in the reaction mixture. Thereafter, in the manner previously described, the thiepinol intermediate was recovered by adding water to the mixture, subjecting the mixture to reduced pressure, adding ether and extracting therewith, washing and drying the ether solution, filtering the drying agent and vaporizing the ether to obtain an oily residue of 6,11-dihydrodibenzo[b,d]thiepin-11-ol.

5 milliliters of thionyl chloride were added to a solution of the oily residue in 30 milliliters of benzene and the resulting mixture heated at reflux temperature for one and one-half hours to obtain a 11-chloro-6,11-dihydrodibenzo[b,e]thiepine intermediate. The intermediate was purified by repeated additions of benzene followed by codistilling the thionyl chloride with benzene under reduced pressure.

The 11-chloro-thiepine intermediate then was added to a solution of 2.5 grams (25 millimoles) of 1-methylpiperazine in 5 milliliters of dimethylformamide and the mixture stirred overnight to obtain a product in the reaction mixture. Water and saturated sodium carbonate solution were added to the reaction mixture and the mixture extracted with toluene, the toluene solution was washed and dried, then subjected to reduced pressure to obtain a 1-(6,11-dihydrodibenzo[b,d]thiepin-11-yl)-4-methylpiperazine product as an oil. The product was purified by chromatographing through a Still column employing 3 percent methanol/chloroform as eluant.

Thereafter it was dissolved in acetone and 0.45 gram (39 millimoles) of maleic acid was added to the solution, the solution concentrated to obtain a precipitate of 1-(6,11-dihydrodibenzo[b,e]thiepin-11-yl)-4-methylpiperazine maleate product. The maleate product had the following elemental analyses:

Calc'd for $C_{19}H_{22}N_2S \cdot C_4H_4O_4$: C, 64.76; H, 6.15; N, 6.57. Found: C, 64.51; H, 6.22; N, 6.55.

EXAMPLE XIII 1-(10,11-Dihydro-3-methoxy-5H-dibenzo[a,d]cyclohepten-5-yl)-4-methylpiperazine

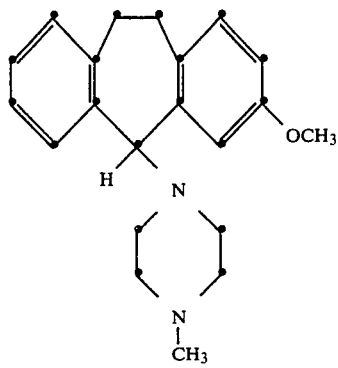

In a manner similar to that described in the preceding examples, 0.5 gram (13 millimoles) of sodium borohydride was added to a solution of 1 gram (43 millimoles) of 10,11-dihydro-3-methoxy-5H-dibenzo[a,d]cyclohepten-5-one in 20 milliliters of ethanol with an added drop of 40 percent sodium hydroxide solution and the mixture heated overnight to obtain 10,11-dihydro-3-methoxy-5H-dibenzo[a,d]cyclohepten-5-ol (5-hydroxy intermediate compound) in the reaction mixture.

The 5-hydroxy intermediate compound was recovered in a manner similar to that previously described and then dissolved in 70 milliliters of benzene. 4 milliliters of thionyl chloride was added thereto and the mixture heated at reflux temperature for 1.5 hours to obtain a 5-chloro-10,11-dihydro-3-methoxy-5H-dibenzo[a,d]cycloheptene (5-chloro intermediate compound) in the reaction mixture which then was recovered as previously described.

The 5-chloro intermediate compound was dissolved in dimethylformamide and mixed with 10 milliliters (1.06 gram, 10 millimoles) of N-methylpiperazine and the mixture stirred overnight at room temperature to obtain a 1-(10,11-dihydro-3-methoxy-5H-dibenzo[a,d]cyclohepten 5-yl)-4-methyl piperazine product. The product was recovered in a manner similar to that previously described and then purified by chromatographing on a silica gel Still column using 3 percent methanol in chloroform as eluant. The eluate was further purified by mixing with n-hexane and concentrating, and triturating with acetonitrile to obtain a purified product, m.p. 119°–119.5° C. Elemental analyses were as follows:

Calc'd for $C_{21}H_{26}N_2O$: C, 78.22; H, 8.13; N, 8.69. Found C, 77.89; H, 8.37; N, 8.60.

EXAMPLE XIV

Ethyl 4-(5H-Dibenzo[a,d]cyclohepten-5-yl)-1-piperazinecarboxylate

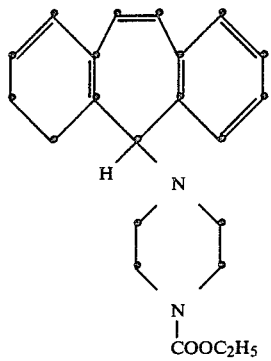

1 gram (44 millimoles) of 5-chloro-5H-dibenzo-[a,d-]cycloheptene prepared in a manner similar to that previously described was added to a solution of 1.4 grams of ethyl N-piperazinecarboxylate in 10 milliliters of dimethylformamide and the resulting mixture allowed to stir overnight at room temperature. At the end of this period, the mixture was subjected to reduced pressure to remove most of the dimethylformamide. Aqueous saturated sodium bicarbonate solution was added, mixed and then extracted with diethyl ether. The ether extract was washed with water and saturated sodium chloride solution, dried over magnesium sulfate, the dried solution subjected to reduced pressure to remove the ether and to obtain the ethyl 4-(5H-dibenzo[a,d]cyclohepten-5-yl)-1-piperazinecarboxylate product as residue. The crude product was treated with and crystallized from acetonitrile. The product after several recrystallizations had a melting point of 159°–160° C. and elemental analyses as follows:

Calc'd for $C_{22}H_{24}N_2O_2$: C, 75.83; H, 6.94; N, 8.04. Found C, 76.17; H, 7.27; N, 7.93.

EXAMPLE XV 4-(5H-Dibenzo[a,d]cyclohepten-5-yl)-1-piperazineethanol

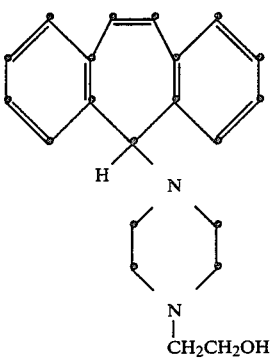

A solution of 1 gram (0.0044 mole) of 5-chloro-5H-dibenzo[a,d]cycloheptene intermediate (prepared in a manner similar to that described in Example I) in 10 milliliters of dimethylformamide and 1.17 grams (0.009 mole) of N-(β-hydroxyethyl) piperazine were stirred together at room temperature for about 24 hours to obtain a 4-(5H-dibenzo[a,d]cyclohepten-5-yl)-1piperazineethanol product in the reaction mixture. The product was recovered in a manner similar to that previously described and purified by chromatographing on a Still column employing 4 percent methanol in chloroform as eluant to obtain an oily residue which on drying at 48° C. and 0.2 millimeter for 18 hours became a solid melting from 107°–108° C. Elemental analyses of the product were as follows:

Calc'd for $C_{21}H_{24}N_2O$ (m.w. 320.4): C, 78.71; H, 7.55; N, 8.75. Found C, 78.52; H, 7.77; N, 9.13.

EXAMPLE XVI

In operations carried out in a manner similar to that above described, the following compounds are prepared: 1-(3-iodo-5H-dibenzo[a,d]cyclohepten-5-yl)-4-methylpiperazine by the reduction of 3-iodo-5H-dibenzo[a,d]cyclohepten-5-one with sodium borohydride to produce 3-iodo-5H-dibenzo[a,d]cyclohepten-5-ol followed by the reaction of the latter with thionyl chloride to obtain 5-chloro-3-iodo-5H-dibenzo[a,d]cycloheptene, then followed by the reaction of the chloro compound with 1-methylpiperazine.

1-(3-Bromo-10,11-dihydro-5H-dibenzo[a,d]cyclohepten-5-yl)-4-methylpiperazine by the reduction of 3-bromo-10,11-dihydro-5H-dibenzo[a,d]cyclohepten-5-one with sodium borohydride to obtain 3-bromo-10,11-dihydro-5H-dibenzo[a,d]cyclohepten-5-ol followed by reaction of the latter with thionyl chloride to obtain 3-bromo-5-chloro-10,11-dihydro-5H-dibenzo[a,d]cycloheptene, then followed by the reaction of the chloro compound with 1-methylpiperazine.

1-(3-Methylthio-10,11-dihydro-5H-dibenzo[a,d]cyclohepten-5-yl)-4-ethylpiperazine by the reduction of 3-methylthio-10,11-dihydro-5H-dibenzo[a,d]cyclohepten-5-one with sodium borohydride to obtain 3-methylthio-10,11-dihydro-5H-dibenzo[a,d]cyclohepten-5-ol followed by the reaction of the latter with thionyl chloride to obtain 5-chloro-3-methylthio-10,11-dihydro-5H-dibenzo[a,d]cycloheptene, then followed by the reaction of the chloro compound with 1-ethylpiperazine.

1-(2-Isopropoxy-6,11-dihydrobenzo[b,e]oxypin-11-yl)-4-(n-butyl)piperazine by the reduction of 2-isopropoxy-6,11-dihydrodibenzo[b,e]oxypin-11-one with sodium borohydride to obtain 2-isopropoxy-6,11-dihydrodibenzo[b,e]oxypin-11-ol followed by the reaction of the latter with thionyl chloride to obtain 11-chloro-2-isopropoxy-6,11-dihydrodibenzo[b,e]oxepine, then followed by the reaction of the chloro compound with 1-(n-butyl)piperazine.

n-Propyl 4-(1,11-dichloro-5H-dibenzo[a,d]cyclohepten-5-yl)-1-piperazinecarboxylate by the reduction of 1,11-dichloro-5H-dibenzo[a,d]cycloheptene-5-one with sodium borohydride to obtain 1,11-dichloro-5H-dibenzo[a,d]cyclohepten-5-ol followed by the reaction of the latter with thionyl chloride to obtain 1,5,11-trichloro-5H-dibenzo[a,d]cycloheptene, then followed by the reaction of the chloro compound with n-propyl N-piperazine carboxylate.

1-(4,11-Difluoro-5,10-dihydrodibenzo[a,d]cycloocten-5-yl)-4-(2-hydroxyethyl)piperazine by the reduction of 4,11-difluoro-5,10-dihydrodibenzo[a,d]cycloocten-5-one to 4,11-difluoro-5,10-dihydrodi[a,d]cycloocten-5-ol followed by the reaction of the latter with thionyl chloride to obtain 5-chloro-4,11-difluoro-5,10-dihydrodibenzo[a,d]cyclooctene, then followed by the reaction of the chloro compound with 1-(2-hydroxyethyl)-piperazine.

EXAMPLE XVII

In reactions carried out in a manner similar to that previously described the following compounds may be prepared.

1-Cinnamoyl-4-(3-methoxy-5H-dibenzo[a,d]cyclohepten-5-yl)piperazine by the reaction of 1-(3-methoxy-5H-dibenzo[a,d]cyclohepten-5-yl)piperazine with cinnamoyl chloride.

1-Cinnamyl-4-(3-methoxy-5H-dibenzo-[a,d]cyclohepten-5-yl)piperazine by the reduction of 1-cinnamoyl-4-(3-methoxy-5H-dibenzo[a,d]cyclohepten-5-yl)piperazine with lithium aluminum hydride.

1-Cinnamoyl-4-(3-methylthio-3H-dibenzo[a,d]cyclohepten-5-yl)piperazine by the reaction of (3-methylthio-3H-dibenzo[a,d]cyclohepten-5-yl)piperazine with cinnamoyl chloride.

1-Cinnamyl-4-(3-methylthio-5H-dibenzo[a,d]cyclohepten-5-yl)piperazine by the reduction of 1-cinnamoyl-4-(3-methylthio-5H-dibenzo[a,d]cyclohepten-5-yl)piperazine with lithium aluminum hydride.

1-(3-Chloro-5H-dibenzo[a,d]cyclohepten-5-yl)-4-cinnamoylpiperazine by the reaction of 1-(3-chloro-5H-dibenzo[a,d]cyclohepten-5-yl)piperazine with cinnamoyl chloride.

1-(3-Chloro-5H-dibenzo[a,d]cyclohepten-5-yl)-4-cinnamylpiperazine by the reduction of 1-(3-chloro-5H-dibenzo[a,d]cyclohepten-5-yl)-4-cinnamoylpiperazine with lithium aluminum hydride.

1-Cinnamoyl-4-(3-chloro-11-bromo-5H-dibenzo[a,d]cyclohepten-5-yl)piperazine by the reaction of 1-(3-chloro-11-bromo-5H-dibenzo[a,d]cyclohepten-5-yl)piperazine with cinnamoyl chloride.

1-Cinnamyl-4-(3-chloro-11-bromo-5H-dibenzo[a,d]cyclohepten-5-yl)piperazine by the reduction of 1-cinnamoyl-4-(3-chloro-11-bromo-5H-dibenzo[a,d]cyclohepten-5-yl)piperazine with lithium aluminum hydride.

1-(6,11-Dihydrodibenzo[b,e]thiepin-11-yl)-4-(3,4,5-trimethoxy)cinnamoylpiperazine by the reaction of 1-(6,11-dihydrodibenzo[b,e]thiepin-11-yl)piperazine with 3,4,5-trimethoxycinnamoyl chloride.

1-(6,11-Dihydrodibenzo[b,e]thiepin-11-yl)-4-(3,4,5-trimethoxycinnamyl)piperazine by the reduction of 1-(6,11-dihydrobenzodi[b,e]thiepin-11-yl)-4-(3,4,5-trimethoxycinnamoyl)piperazine with lithium aluminum hydride.

EXAMPLE XVIII

The salts suitable for use in the compositions of the present invention may be prepared by mixing together the appropriate piperazine compound of Formula I with an appropriate acid in a solvent such as ethanol whereupon the salt forms and precipitates as a crystalline solid. The following salts are prepared:

4-(5H-dibenzo[a,d]cyclohepten-5-yl)-piperazine hydrogen maleate;

1-(3-bromo-5H-dibenzo[a,d]cyclohepten-5-yl)-4-methylpiperazine hydrogen succinate;

1-(3-chloro-5H-dibenzo[a,d]cyclohepten-5-yl)-4-methylpiperazine hydrochloride;

1-(3-methoxy-5H-dibenzo[a,d]cyclohepten-5-yl)-4-methylpiperazine hydrogen phosphate;

1-methyl-4-(3-methylthio-5H-dibenzo-[a,d]cyclohepten-5-yl)piperazine hydrogen maleate;

1-(3-chloro-11-bromo-5H-dibenzo[a,d]cyclohepten-5-yl)-4-methylpiperazine hydrogen malonate;

1-(10,11-dihydro-3-methoxy-5H-dibenzo[a,d]cyclohepten-5-yl)-4-methyl piperazine hydrochloride.

Examples XIX–XXIV illustrate compositions for carrying out the methods of the present invention.

EXAMPLE XIX 10,000 hard gelatin capsules each containing as active ingredient 25 milligrams of 1-cinnamyl-4-(5H-dibenzo[a,d]cyclohepten-5-yl)piperazine are prepared from the following formulation:

|  | Grams |
| --- | --- |
| Active ingredient | 250 |
| Lactose | 750 |
| Starch | 250 |
| Talc | 250 |
| Calcium stearate | 10 |

A uniform mixture of the active and supplementary ingredients is prepared and filled into two-piece hard gelatin capsules. The capsules are suitable for oral administration to provide therapeutic relief for patients with cardiovascular disorders by alleviating cardiac arrhythmias and/or peripheral vasoconstriction.

EXAMPLE XX

Capsules are made by substituting for 1-cinnamyl-4-(5H-dibenzo[a,d]cyclohepten-5-yl)piperazine in the formulation of Example XVIII one of the following:

(1) 1-cinnamyl-4-(3-bromo-5H-dibenzo[a,d]cyclohepten-5-yl)piperazine;

(2) 1-(3-chloro-5H-dibenzo[a,d]cyclohepten-5-yl)-4-methylpiperazine;

(3) 1-(3-methoxy-5H-dibenzo[a,d]cyclohepten-5-yl)-4-methylpiperazine;

(4) 1-methyl-4-(3-methylthio-5H-dibenzo[a,d]cyclohepten-5-yl)piperazine;

(5) 1-(5H-dibenzo[a,d]cyclohepten-5-yl)-4-methylpiperazine.

EXAMPLE XXI 5000 compressed tablets, each containing as active ingredient 10 milligrams of 1-cinnamyl-4-(5H-dibenzo[a,d]cyclohepten-5-yl)piperazine are prepared from the following formulation:

|  | Grams |
| --- | --- |
| Active ingredient | 50 |
| Starch | 70 |
| Dibasic calcium phosphate hydrous | 500 |
| Calcium stearate | 2.5 |

The ingredients are finely powdered, mixed well, and then granulated with 10 percent starch paste. The granulation is dried and compressed into tablets using starch as a disintegrant and calcium stearate as lubricant.

EXAMPLE XXII

One liter of a parenteral suspension comprising 5-milligrams of 1-(3-bromo-5H-dibenzo[a,d]cyclohepten-5-yl)-4-methylpiperazine as active ingredient per milliliter is prepared from the following formulation:

|  | Grams |
| --- | --- |
| Active ingredient | 5.0 |
| Polysorbate 80 | 2.0 |
| Sodium chloride | 9.0 |
| Sodium carboxymethyl cellulose | 10.0 |
| Methyl paraben | 1.8 |
| Propyl paraben | 0.2 |
| Water for injection, U.S.P. q.s. to 1 liter | |

The parabens, sodium chloride and carboxymethyl cellulose are dissolved in one-half the total volume of water by heating to 95° C. to obtain a solution which is then filtered and autoclaved. The polysorbate is dissolved in one-third of the total volume of water, and the resulting solution also filtered and autoclaved. Sterile active ingredient is added to the second solution and the mixture passed through a sterile colloid mill to obtain a suspension of active ingredient. The first solution is added to the suspension with stirring then U.S.P. water added to 1 liter. Sterile vials are filled with the suspension while stirring.

EXAMPLE XXIII

Five liters of an oral suspension comprising 25 milligrams of 1-(5H-dibenzo[a,d]cyclohepten-5-yl)-4-methylpiperazine per 5 milliliters (teaspoonful) are prepared from the following formulation:

|  | Grams |
| --- | --- |
| Active ingredient | 25.0 |
| Sucrose | 300.0 |
| Dioctyl sodium sulfosuccinate | 0.5 |
| Bentonite | 22.5 |
| Methyl paraben | 7.5 |
| Propyl paraben | 1.5 |
| Antifoam A.F. Emulsion | 0.15 |
| Propylene glycol | 52.0 |
| FD&C Yellow #5 | 0.1 |
| Sodium cyclamate | 50.0 |
| Sodium saccharin | 5.0 |
| Orange flavor | 7.5 |
| Filtered purified water, q.s. to 5 liters | |

The parabens are dissolved in propylene glycol and this solution is added to a solution containing sodium cyclamate, sodium saccharin and sucrose in half the volume of water. The bentonite is then suspended in hot (about 85° C.) water and stirred for 60 minutes and the resulting suspension added to the first solution.

The sulfosuccinate is then dissolved in some water and the active ingredient (A.I.) suspended therein. The antifoam emulsion is diluted to somewhat viscous but pourable (lotionlike) consistency and then is added to the suspension and mixed.

The suspension containing active ingredient is then added to the first mixture and stirred, then color and flavoring added, the resulting mixture diluted to volume with water and stirred to a homogeneous mixture. The mixture is then passed through a colloidal mill and used to fill suitable containers.

EXAMPLE XXIV

Gelatin capsules are prepared in separate operations carried out in a manner similar to that described in Example XIX but substituting for the active ingredient other compounds having the formula represented by Formula I as follows:

(1) 4-(5H-dibenzo[a,d]cyclohepten-5-yl)piperazine;
(2) 1-(3-chloro-11-bromo-5H-dibenzo[a,d]cyclohepten-5-yl)-4-methylpiperazine;
(3) 1-(6,11-dihydrodibenzo[b,e]thiepin-11-yl)-4-methylpiperazine maleate;
(4) 1-(10,11-Dihydro-3-methoxy-5H-dibenzo[a,d]cyclohepten-5-yl)-4-methylpiperazine;
(5) Ethyl 4-(5H-dibenzo[a,d]cyclohepten-5-yl)-1-piperazinecarboxylate.

What is claimed is:

1. A composition useful for the treatment of cardiovascular disorders caused by high cellular concentration of Ca$^{++}$ comprising a therapeutically effective amount of a compound having the formula:

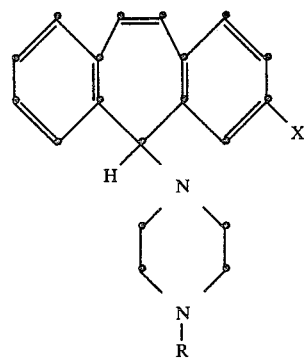

wherein
X is hydrogen, halogen, lower alkoxy, lower alkylthio, lower alkylsulfonyl, or trifluoromethyl,
R is cinnamyl, lower alkoxycinnamyl, cinnamoyl, lower alkoxycinnamoyl, lower hydroxyalkyl or carbalkoxy;
or a pharmaceutically acceptable acid addition salt thereof; said compound in admixture with a pharmaceutically acceptable carrier.

2. A composition according to claim 1 wherein the compound is 1-cinnamyl-4-(5H-dibenzo[a,d]cyclohepten-5-yl)piperazine.

3. A method for treating cardiovascular disorders caused by high cellular concentration of Ca$^{++}$ comprising administering to a patient in need of such treatment, a therapeutically effective amount of a compound having the formula:

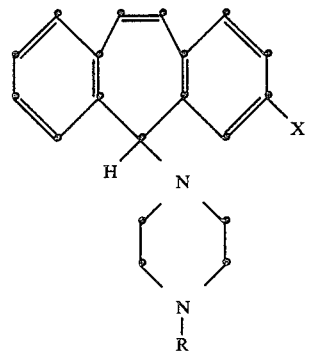

wherein

X is hydrogen, halogen, lower alkoxy, lower alkylthio, lower alkylsulfonyl, or trifluoromethyl, R is hydrogen, lower alkyl, cinnamyl, lower alkoxycinnamyl, cinnamoyl, lower alkoxycinnamoyl, lower hydroxyalkyl, or carbalkoxy;

or a pharmaceutically acceptable acid addition salt thereof.

4. The method according to claim 3 wherein the compound is 1-(3-bromo-5H-dibenzo a,d, cyclohepten-5-yl)-4-methylpiperazine.

5. The method according to claim 3 wherein the compound is 1-(3-chloro-5H-dibenzo a,d -cyclohepten-5-yl)-4-methylpiperazine.

6. The method according to claim 3 wherein the compound is one in which X is alkoxy and R is methyl.

7. The method according to claim 6 wherein the compound is 1-(3-methoxy-5H-dibenzo[a,d]cyclohepten-5-yl)-4-methylpiperazine.

8. The method according to claim 3 wherein the compound is one in which X is alkylthio and R is methyl.

9. The method according to claim 8 wherein the compound is 1-methyl-4-(3-methylthio-5H-dibenzo[a,d]-cyclohepten-5-yl)piperazine.

* * * * *